United States Patent
Clowers

(10) Patent No.: US 6,698,427 B1
(45) Date of Patent: Mar. 2, 2004

(54) COMFORT RING FOR PATIENT MEDICAL MASK

(76) Inventor: Liselle K. Clowers, 2035 Julian La., Clayton, NC (US) 27520

(*) Notice: Subject to any disclaimer, the term of this patent is extended or adjusted under 35 U.S.C. 154(b) by 0 days.

(21) Appl. No.: 10/223,866

(22) Filed: Aug. 20, 2002

(51) Int. Cl.$^7$ ............................................... A62B 18/00
(52) U.S. Cl. ........................... 128/206.21; 128/200.24; 128/202.13; 128/205.25; 128/206.28
(58) Field of Search .......... 128/200.24, 201.22–202.11, 128/202.28, 203.28, 203.29, 204.18, 205.13, 205.17, 205.25, 205.27–207.18, 202.13, 849, 856; 150/154–168, 901; 206/38, 305, 349, 438

(56) References Cited

U.S. PATENT DOCUMENTS

| | | |
|---|---|---|
| 2,127,136 A | 8/1938 | Pobirs |
| 4,038,979 A | 8/1977 | McCosker |
| 4,201,205 A | 5/1980 | Bartholomew |
| 4,337,767 A | 7/1982 | Yahata |
| 4,579,113 A | 4/1986 | McCreadie et al. |
| 5,040,530 A | 8/1991 | Bauer et al. |
| 5,155,863 A | 10/1992 | Roberts |
| D351,226 S | 10/1994 | Parvatharaj |
| 5,429,125 A | 7/1995 | Wagner et al. |
| 5,492,114 A | 2/1996 | Vroman |
| 5,538,001 A | 7/1996 | Bridges |
| 5,586,551 A | 12/1996 | Hilliard |
| 5,623,923 A * | 4/1997 | Bertheau et al. ........ 128/207.11 |
| D411,297 S | 6/1999 | Rosiello et al. |
| 5,909,732 A * | 6/1999 | Diesel et al. ........... 128/206.24 |
| 5,918,598 A * | 7/1999 | Belfer et al. ........... 128/206.25 |
| 6,041,782 A | 3/2000 | Angadjivand et al. |
| 6,386,198 B1 | 5/2002 | Rugless |

* cited by examiner

*Primary Examiner*—Glenn K. Dawson
(74) *Attorney, Agent, or Firm*—Coats & Bennett, P.L.L.C.

(57) ABSTRACT

A medical mask assembly includes a medical mask and a comfort ring releasably mated to the mask. The mask includes a interior surface and an exterior surface and a mating edge where the two meet. The comfort ring includes a strip of cloth and two elastic members secured to the cloth, and is formed in the shape of an annular ring with a central aperture therethrough. When mated to the mask, the comfort ring is disposed so as to cover substantially all of the mating edge with one elastic member proximate the interior surface of the medical mask and the other elastic member proximate the exterior surface of the medical mask. As such, the surface touching the patient's face is the outer surface of the comfort ring rather than the interior surface and/or rim edge of the mask. Thus, the patient experiences a surface that is more comfortable.

21 Claims, 3 Drawing Sheets

COMFORT RING FOR PATIENT MEDICAL MASK

BACKGROUND OF THE INVENTION

The present invention relates generally to the field of patient medical masks, such as oxygen masks, and more particularly to an adapter for patient medical masks that helps cushion and/or insulate the mask against the patient's face to reduce discomfort.

Medical masks, such as oxygen masks, anesthesia masks, respiratory therapy masks, and the like, have long been known in the art. Such masks are typically either made from a somewhat pliable material and/or include a rim of soft rubber-like material. While such masks have proven medically useful, they have also proven to be uncomfortable to some patients, particularly for long-term use. This is particularly true as many potential measures that could be taken to increase patient comfort may be seen as impeding the critically important operational aspects of the medical mask related to its medical function(s).

As such, there remains a need to improve the comfort level of patient medical masks, particularly for long-term use.

SUMMARY OF THE INVENTION

A medical mask assembly of the present invention includes a medical mask and a comfort ring. The medical mask includes an interior surface and an exterior surface and a mating edge where the two meet. The mask is adapted to be applied to a patient's face proximate the mating edge. The comfort ring includes a portion of cloth material and two elastic members secured to the cloth material. The cloth is formed in the shape of an annular ring with a central aperture therethrough. The cloth includes an inner surface and a preferably soft outer surface, with the inner and outer surfaces meeting at first and second inner edges that generally bound the aperture. One elastic member is secured to the cloth proximate the first inner edge and extends substantially the entire length of the first inner edge. The other elastic member is secured to the cloth proximate the second inner edge and extends substantially the entire length of the second inner edge. The comfort ring is removably mated to the medical mask; and, when mated to the mask, is disposed so as to cover substantially all of the mating edge with one elastic member proximate the interior surface of the medical mask and the other elastic member proximate the exterior surface of the medical mask. As such, the surface touching the patient's face is the outer surface of the comfort ring rather than the interior surface and/or rim edge of the mask. Thus, the patient experiences a surface that is softer and/or insulated from the medical mask, and therefore more comfortable.

The reliance on elastic members to mate the comfort ring to the mask allows for the comfort ring to be readily removed therefrom, such as for cleaning and/or replacement. Further, the shape of the comfort ring means that the operations of the medical mask are unaffected by having the comfort ring attached. As such, the medical functions of the mask will be unaffected even when highly untrained personnel, such as family members, add or remove the comfort ring.

DESCRIPTION OF THE PREFERRED EMBODIMENTS

Figure 1:
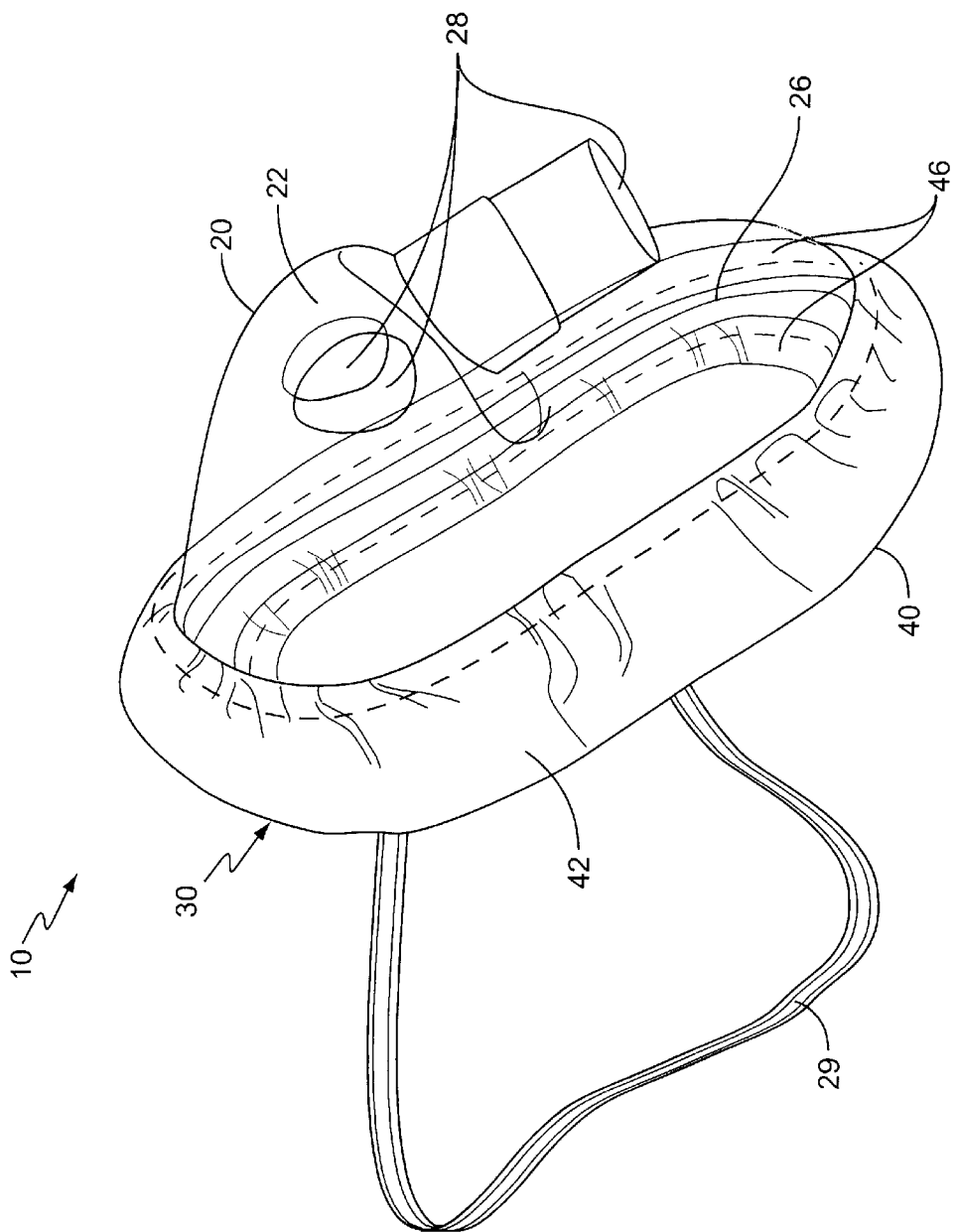
FIG. 1 shows one embodiment of the medical mask assembly of the present invention.
Figure 2:
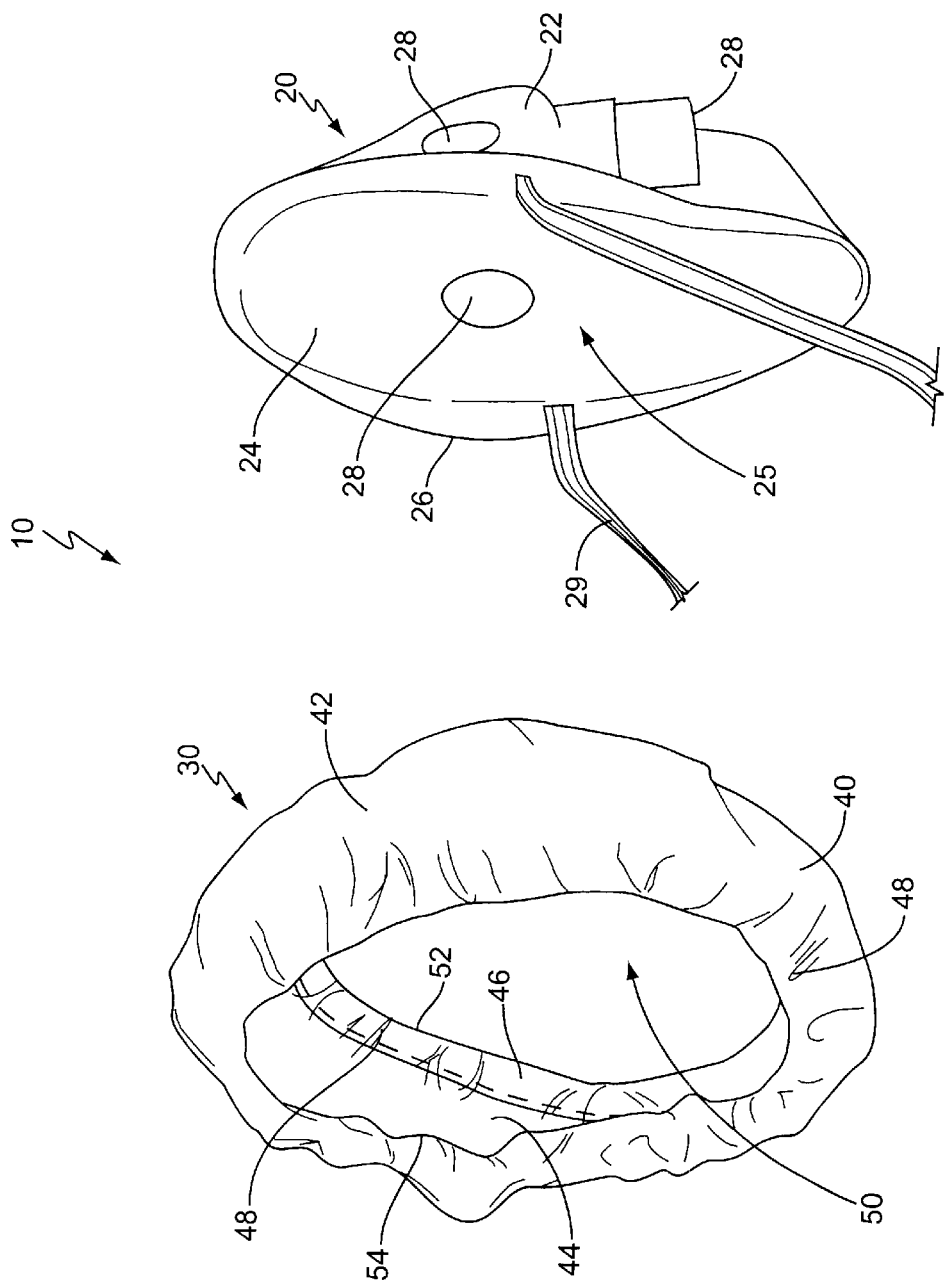
FIG. 2 shows a partially exploded view of the medical mask assembly of FIG. 1.

One embodiment of a medical mask assembly 10 according to the present invention is shown in FIG. 1. The medical mask assembly 10 includes a medical mask 20 and a comfort ring 30 removably attached thereto. The medical mask 20 may take any form known in the art that allows for a desired gas to be supplied to the mask 20 and for exhaled gases to be exhausted from the mask 20. Examples of commercially available masks suitable for the present invention include without limitation, model 1083 oxygen/aerosol masks from Hudson RCI of Temecula, Calif. Generically, the mask 20 includes an exterior surface 22, an interior space 25 bounded by an interior surface 24, a mating (or rim) edge 26 at the boundary between the exterior surface 22 and the interior surface 24, and a plurality of ports 28 providing inputs to and/or exhausts from the interior space 25. The mask 20 may advantageously be made from a clear, pliable material. As is known in the art, the mask 20 is designed to be placed over the patient's face, with the interior space 25 facing the patient, with a slightly air-tight seal formed between the interior surface 24 proximate the rim edge 26 and the patient's face. The mask 20 may simply be placed on the patient's face, or may be held in place with the aid of one or more suitable straps 29. Various gases (e.g., oxygen, respiratory therapy mists, etc.) are then supplied to the patient via one or more of the ports 28, typically inhaled by the patient, with the exhaled gases exhausting though one or more other ports 28.

The present invention improves on prior art medical masks by, inter alia, adding a cushioning ring 30 that overlays the rim edge 26 of the mask 20 and provides a better surface for direct contact with the patient's face, without interfering with the medical functions of the mask 20. Further, this comfort ring 30 is advantageously removably attached to the medical mask 20, as is discussed further below. The better surface provided by the comfort ring 30 may be "better" in that it is softer than the material of the medical mask 30, or it may be "better" in that is more insulating (and therefore feels warmer) than the material of the medical mask 30, or both.

Figure 3:
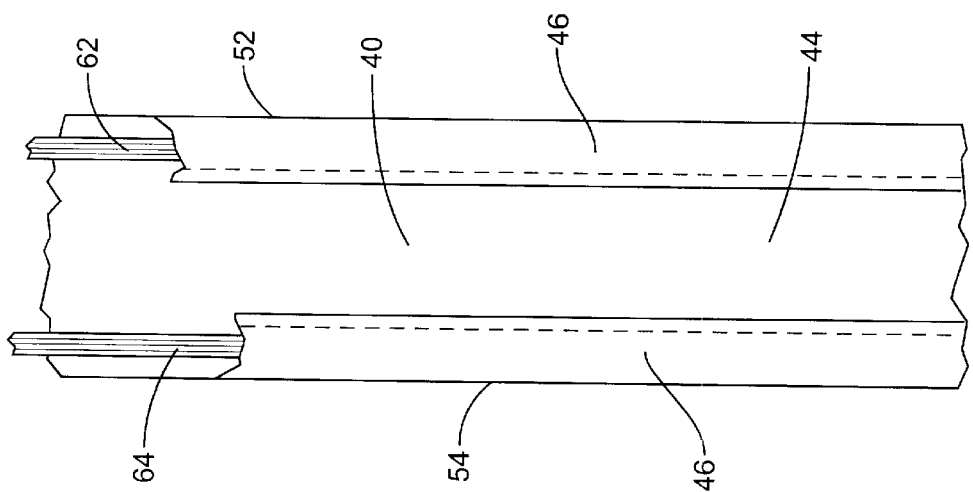
FIG. 3 shows a partial section of the comfort ring shown in FIG. 1, partially cut away to show the elastic members.

The comfort ring 30 includes a plurality of elastic members 62,64 and a cloth material 40 extending between the elastic members 62,64. The cloth material preferably takes the form of a strip of cloth 40 formed in the shape of an annular ring and defining an annular trough, with an aperture 50 in the center of the ring. For purposes of description, the surface of the cloth 40 facing the aperture 50 is referred to as the inner surface 44, while the opposing surface is the outer surface 42. It is preferred that the outer surface 42 of the cloth 40 have a soft-to-the-touch texture, such as a felt-like texture. Of course, both surfaces 42,44 of the cloth 40 may have such a texture, but this is not required. As can be seen in the Figures, the inner surface 44 meets the outer surface 42 at two edges 52,54, which are referred to herein as inner edges as they help bound the aperture 50. The cloth 40 is preferably folded over and stitched in place proximate these inner edges 52,54 so as to form respective pockets that help contain the elastic members 62,64 (see FIG. 3). The elastic members 62,64 may take the form of elastic bands with their respective ends tied together to form a ring or hoop.

Preferably, the cloth strip 40 between the elastic members 62,64 has a free length slightly larger than the free length of the elastic members 62,64. As such, the elastic members 62,64 pull against the cloth 40 along the corresponding inner edge thereof, resulting in a series of gatherings 48 along the inner edges 52,54. In this arrangement, the aperture 50 of the comfort ring 30 can be readily expanded slightly, such as to size having a perimeter that matches the free length of the cloth 40, and will naturally spring back to the shorter length along the inner edges 52,54 when released due to the action of the elastic members 62,64.

To form the mask assembly 10, the comfort ring 30 is slipped over the rim edge 26 of the medical mask 20, so that one inner edge 52 is disposed proximate the inner surface 24 of the mask 20 and the other inner edge 54 is disposed proximate the outer surface 22 of the mask 20, and then released. The elastic members 62,64 will cause the inner edges 52,54 of the comfort ring 30 to pull inwards against the medical mask 20, thereby releasably mating the comfort ring 30 to the mask 20. The amount of overlap between the comfort ring 30 and the mask 20 is determined by the width of the ring 30—the path length distance between the inner edges 52,54 along the cloth 40. The greater the width, the greater the amount of overlap, with a width of approximately 1½ inches being particularly advantageous. Whatever the width of the comfort ring 30, it should not extend along the interior or exterior surfaces 22,24 of the mask 20 so far as to interfere with any of the ports 28 on the medical mask 20.

With the comfort ring 30 mated to the mask 20, the rim edge of the mask 20 is covered by the comfort ring 30. As such, the surface touching the patient's face is the outer surface 42 of the comfort ring 30 rather than the interior surface 24 and/or rim edge 26 of the mask 20. Thus, the patient experiences a surface that is softer and/or insulated from the medical mask, and therefore more comfortable.

Note that relying on the elastic members 62,64 to mate the comfort ring 30 to the mask 20 allows for the comfort ring 30 to be readily removed therefrom, such as for cleaning and/or replacement. Note further that the attachment and removal of the comfort ring 30 to/from the mask 20 can be easily accomplished without any risk of damage to the mask 20, and that the operations of the mask 20 with the comfort ring 30 attached are unaffected thereby. As such, the medical functions of the mask 20 will be unaffected even when highly untrained personnel, such as family members, add or remove the comfort ring 30.

The discussion above has described the shape of the comfort ring 30 as being annular. It should be noted that the term "annular" is not meant to imply a exact circular ring shape, but instead a generally round ring-like shape that may actually be an oval, an ellipse, a loose rectangle, etc., or any rough approximation thereof, provided there is a central passage 25 through the general center thereof. Further, the term "annular," as used herein does not require complete 360° coverage; instead, a small gap (e.g., less than 10° of arc) may exist such as when the edges of the cloth 40 are placed close together, but not sewn together.

The discussion above has described the primary material of the comfort ring 30 as "cloth," however cloth in the traditional sense is not required. Indeed, the primary material of the comfort ring 30 may be cotton, rayon, felt, paper, or reinforced paper (e.g., TYVEK material), or any other flexible material without substantial elastic properties (e.g., excluding neoprene, rubber, etc.). The term "cloth" as used herein should be construed accordingly, with the term "fabric" being used for traditional materials such as cotton, rayon, etc. The choice of primary material for the comfort ring 30 may depend on the desired application; for instance, one-use disposable comfort rings 30 may be made from paper for lower cost, while reusable single-patient comfort rings 30 may be made from washable cotton or synthetic felt-like fabric.

While the invention has been illustrated and described in detail in the drawings and foregoing description, the same is to be considered as illustrative and not restrictive in character, it being understood that only some embodiments have been shown and described and that all changes and modifications that come within the meaning and equivalency range of the appended claims are intended to be embraced therein.

What is claimed is:

1. A medical mask assembly, comprising:
    a medical mask adapted to be applied to a patient's face proximate a mating edge and having an interior surface and an exterior surface;
    a comfort ring comprising:
        cloth formed in the shape of an annular ring with a central aperture therethrough, the cloth having an inner surface and a soft outer surface; said inner and outer surfaces meeting at first and second inner edges that generally bound said aperture;
        a first elastic member secured to said cloth proximate said first inner edge;
        a second elastic member secured to said cloth proximate said second inner edge;
    said comfort ring removably mated to said medical mask and disposed so as to cover substantially all of said mating edge with said first elastic member proximate said interior surface of said medical mask and said second elastic member proximate said exterior surface of said medical mask.

2. The assembly of claim 1 wherein said aperture of said comfort ring allows substantially free access to an interior space of said medical mask.

3. The assembly of claim 1 wherein said first and second elastic members comprise elastic bands.

4. The assembly of claim 3 wherein said cloth includes pockets disposed proximate said first and second inner edges, and wherein said first and second elastic members extend through respective said pockets.

5. The assembly of claim 4 wherein said pockets extend along substantially all of said first and second inner edges.

6. The assembly of claim 1 wherein said cloth is felt.

7. The assembly of claim 1 wherein said first elastic member extends substantially the entire length of said first inner edge, and wherein said second elastic member extends substantially the entire length of said second inner edge.

8. The assembly of claim 1 wherein:
    said aperture of said comfort ring allows substantially free access to an interior space of said medical mask;
    said cloth includes pockets disposed proximate said first and second inner edges;
    said first elastic member comprises a first elastic band extending substantially the entire length of said first inner edge and extending through at least one of said pockets; and
    said second elastic member comprises a second elastic band extending substantially the entire length of said second inner edge and extending through at least another of said pockets.

9. The assembly of claim 8 wherein said cloth is felt.

10. The assembly of claim 8 wherein said cloth further has a trough cross-section.

11. The assembly of claim 1 wherein said cloth further has a trough cross-section.

12. The assembly of claim 1 wherein said cloth further has a trough cross-section, wherein said first elastic member extends substantially the entire length of said first inner edge, and wherein said second elastic member extends substantially the entire length of said second inner edge.

13. A method of using medical mask assembly, comprising:

provides a medical mask adapted to be applied to a patient's face proximate a mating edge and having an interior surface and an exterior surface;

providing a comfort ring comprising:

cloth formed in and annular shape with a central aperture therethrough, the strip of cloth having an inner surface and a soft outer surface; said inner and outer surfaces meeting at first and second inner edges that generally bound said aperture;

a first elastic member secured to said cloth proximate said first inner edge;

a second elastic member secured to said cloth proximate said second inner edge;

removably mating said comfort ring to said medical mask such that said comfort ring substantially covers all of said mating edge with said first elastic member proximate said interior surface of said medical mask and said second elastic member proximate said exterior surface of said medical mask.

14. The method of claim 13 wherein with said aperture of said comfort ring allows substantially free access to an interior space of said medical mask when mated thereto.

15. The method of claim 13 wherein said first and second elastic members comprise elastic bands.

16. The method of claim 15 wherein said first and second elastic members comprise elastic bands substantially captured within respective pockets of said cloth.

17. The method of claim 13 wherein said first elastic member extends substantially the entire length of said first inner edge, and wherein said second elastic member extends substantially the entire length of said second inner edge.

18. The method of claim 13 further comprising placing said medical mask with said comfort ring mated thereto on a patient's face such that said cloth provides facial insulation from said medical mask to the patient.

19. The method of claim 13 wherein:

said cloth includes pockets disposed proximate said first and second inner edges;

said first elastic member comprises a first elastic band extending substantially the entire length of said first inner edge and extending through at least one of said pockets;

said second elastic member comprises a second elastic band extending substantially the entire length of said second inner edge and extending through at least another of said pockets; and said aperture of said comfort ring allows substantially free access to an interior space of said medical mask when said comfort ring is mated to said medical mask.

20. The method of claim 19 wherein said cloth further has a trough cross-section, and wherein removably mating said comfort ring to said medical mask such that said comfort ring substantially covers all of said mating edge comprises removably mating said comfort ring to said medical mask such that said mating edge is disposed in said trough.

21. The method of claim 13 wherein said first elastic member extends substantially the entire length of said first inner edge, wherein said second elastic member extends substantially the entire length of said second inner edge, wherein said cloth further has a trough cross-section, and wherein removably mating said comfort ring to said medical mask such that said comfort ring substantially covers all of said mating edge comprises removably mating said comfort ring to said medical mask such that said mating edge is disposed in said trough.

\* \* \* \* \*